United States Patent
Dinville et al.

(10) Patent No.: US 9,173,745 B2
(45) Date of Patent: Nov. 3, 2015

(54) INSTRUMENTS AND METHODS FOR REMOVING FIXATION DEVICES FROM INTERVERTEBRAL IMPLANTS

(75) Inventors: Hervé Dinville, St. Parres aux Tertres (FR); Samuel Lequette, Toulouse (FR); Emmanuel Bougère, Troyes (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 13/158,761

(22) Filed: Jun. 13, 2011

(65) Prior Publication Data

US 2012/0116466 A1    May 10, 2012

Related U.S. Application Data

(63) Continuation-in-part of application No. PCT/IB2009/008048, filed on Dec. 31, 2009.

(51) Int. Cl.
*A61B 17/58* (2006.01)
*A61B 17/60* (2006.01)
(Continued)

(52) U.S. Cl.
CPC ............. *A61F 2/442* (2013.01); *A61B 17/7074* (2013.01); *A61F 2/447* (2013.01);
(Continued)

(58) Field of Classification Search
CPC .................. A61F 2/4611; A61F 2/442; A61F 2002/4475; A61F 2220/0025; A61F 2002/30785; A61F 2002/30787; A61F 2002/30578; A61F 2002/30782; A61F 2/447; A61F 2/30579; A61F 2002/30576; A61F 2002/30403; A61F 2002/30889; A61F 2002/30604; A61F 2220/0041; A61F 2002/30879; A61F 2002/30428; A61F 2002/3041; A61F 2002/30472
USPC ........... 606/86 A, 86 B, 90, 96–99, 914–916; 623/17.11–17.16
See application file for complete search history.

(56) References Cited

U.S. PATENT DOCUMENTS

| 344,683 A | 6/1886 | Sherer |
| 1,025,596 A | 5/1912 | Strawser |

(Continued)

FOREIGN PATENT DOCUMENTS

| DE | 20320454 | 10/2004 |
| DE | 10323363 | 12/2004 |

(Continued)

OTHER PUBLICATIONS

World Intellectual Property Organization; International Search Report and Written Opinion of the International Searching Authority for International App. No. PCT/IB2007/000367, PCT Pub'n. No. WO2007093900; Oct. 22, 2007; WIPO; Geneva, Switzerland; all pages.

(Continued)

*Primary Examiner* — Christopher Beccia
*Assistant Examiner* — Diana S Jones
(74) *Attorney, Agent, or Firm* — Denko Coburn Lauff LLP

(57) ABSTRACT

Anchor removal instruments and methods for using the instruments are provided. In some embodiments, an intervertebral implant anchor extractor tool comprises a support, a support retainer configured to hold the support fixed with respect to the implant, an extractor having an anchor retainer, and an extractor guide. An embodiment of a method of using this implant anchor extractor tool comprises the steps of obtaining access to an anchor, grasping the anchor, and applying a withdrawal force on the anchor while applying a countervailing force against the implant or a vertebral structure.

23 Claims, 12 Drawing Sheets

(51) Int. Cl.
    *A61F 2/00*    (2006.01)
    *A61F 2/44*    (2006.01)
    *A61F 2/46*    (2006.01)
    *A61B 17/70*   (2006.01)
    *A61F 2/30*    (2006.01)

(52) U.S. Cl.
    CPC .... *A61F 2/4611* (2013.01); *A61F 2002/30401* (2013.01); *A61F 2002/30403* (2013.01); *A61F 2002/30428* (2013.01); *A61F 2002/30472* (2013.01); *A61F 2002/30576* (2013.01); *A61F 2002/30578* (2013.01); *A61F 2002/30579* (2013.01); *A61F 2002/30604* (2013.01); *A61F 2002/30782* (2013.01); *A61F 2002/30785* (2013.01); *A61F 2002/30787* (2013.01); *A61F 2002/30879* (2013.01); *A61F 2002/30889* (2013.01); *A61F 2002/4475* (2013.01); *A61F 2220/0025* (2013.01); *A61F 2220/0041* (2013.01)

(56) References Cited

U.S. PATENT DOCUMENTS

| | | | |
|---|---|---|---|
| 1,121,484 | A | 12/1914 | Crites |
| 4,135,506 | A | 1/1979 | Ulrich |
| 5,197,986 | A | 3/1993 | Mikhail |
| 5,314,477 | A | 5/1994 | Marnay |
| 5,358,526 | A | 10/1994 | Tornier |
| 5,397,364 | A | 3/1995 | Kozak et al. |
| 5,401,269 | A | 3/1995 | Buttner-Janz et al. |
| 5,443,514 | A * | 8/1995 | Steffee .................. 128/898 |
| 5,522,845 | A | 6/1996 | Wenstrom, Jr. |
| 5,571,109 | A | 11/1996 | Bertagnoli |
| 5,713,899 | A | 2/1998 | Marnay et al. |
| 6,045,552 | A | 4/2000 | Zucherman et al. |
| 6,059,787 | A | 5/2000 | Allen |
| 6,063,121 | A | 5/2000 | Xavier et al. |
| 6,143,032 | A | 11/2000 | Schafer et al. |
| 6,174,311 | B1 | 1/2001 | Branch et al. |
| 6,179,873 | B1 | 1/2001 | Zientek |
| 6,235,059 | B1 | 5/2001 | Benezech et al. |
| 6,241,769 | B1 | 6/2001 | Nicholson et al. |
| 6,342,074 | B1 | 1/2002 | Simpson |
| 6,344,057 | B1 | 2/2002 | Rabbe et al. |
| 6,368,350 | B1 | 4/2002 | Erickson et al. |
| 6,419,706 | B1 | 7/2002 | Graf |
| 6,447,546 | B1 | 9/2002 | Bramlet et al. |
| 6,482,233 | B1 | 11/2002 | Aebi et al. |
| 6,506,216 | B1 | 1/2003 | McCue et al. |
| 6,540,753 | B2 * | 4/2003 | Cohen ..................... 606/99 |
| 6,558,424 | B2 | 5/2003 | Thalgott |
| 6,610,093 | B1 | 8/2003 | Pisharodi |
| 6,770,096 | B2 | 8/2004 | Bolger et al. |
| 6,899,735 | B2 | 5/2005 | Coates et al. |
| 6,936,071 | B1 | 8/2005 | Marnay et al. |
| 6,964,687 | B1 | 11/2005 | Bernard et al. |
| 6,994,727 | B2 | 2/2006 | Khandkar et al. |
| 7,060,097 | B2 | 6/2006 | Fraser et al. |
| 7,153,325 | B2 | 12/2006 | Kim et al. |
| 7,204,852 | B2 | 4/2007 | Marnay et al. |
| 7,232,463 | B2 | 6/2007 | Falahee |
| 7,594,931 | B2 | 9/2009 | Louis et al. |
| 7,695,516 | B2 | 4/2010 | Zeegers |
| 7,771,478 | B2 | 8/2010 | Navarro et al. |
| 7,998,211 | B2 | 8/2011 | Baccelli et al. |
| 8,075,618 | B2 | 12/2011 | Trieu et al. |
| 8,147,556 | B2 | 4/2012 | Louis et al. |
| 8,241,359 | B2 | 8/2012 | Davis et al. |
| 8,267,999 | B2 | 9/2012 | Beaurain et al. |
| 8,313,528 | B1 | 11/2012 | Wensel |
| 8,343,219 | B2 | 1/2013 | Allain et al. |
| 8,349,015 | B2 | 1/2013 | Bae et al. |
| 2002/0070565 | A1 | 6/2002 | Szapucki et al. |
| 2002/0165613 | A1 | 11/2002 | Lin et al. |
| 2003/0069640 | A1 | 4/2003 | Ferreira et al. |
| 2003/0109928 | A1 | 6/2003 | Pasquet et al. |
| 2003/0195514 | A1 | 10/2003 | Trieu et al. |
| 2004/0117022 | A1 | 6/2004 | Marnay et al. |
| 2004/0143332 | A1 | 7/2004 | Krueger et al. |
| 2004/0153157 | A1 | 8/2004 | Keller |
| 2004/0199254 | A1 | 10/2004 | Louis et al. |
| 2004/0243238 | A1 | 12/2004 | Arnin et al. |
| 2004/0243240 | A1 | 12/2004 | Beaurain et al. |
| 2005/0027359 | A1 | 2/2005 | Mashburn |
| 2005/0060034 | A1 | 3/2005 | Berry et al. |
| 2005/0065611 | A1 | 3/2005 | Huppert et al. |
| 2005/0085917 | A1 | 4/2005 | Marnay et al. |
| 2005/0096745 | A1 | 5/2005 | Andre et al. |
| 2005/0143733 | A1 | 6/2005 | Petit |
| 2005/0149189 | A1 | 7/2005 | Mokhtar et al. |
| 2006/0069437 | A1 | 3/2006 | Weber |
| 2006/0121084 | A1 | 6/2006 | Borden et al. |
| 2006/0122703 | A1 | 6/2006 | Aebi et al. |
| 2006/0136063 | A1 | 6/2006 | Zeegers |
| 2006/0142863 | A1 | 6/2006 | Fraser et al. |
| 2006/0155377 | A1 | 7/2006 | Beaurain et al. |
| 2006/0235426 | A1 | 10/2006 | Lim et al. |
| 2007/0073404 | A1 | 3/2007 | Rashbaum et al. |
| 2007/0260249 | A1 | 11/2007 | Boyajian et al. |
| 2009/0105832 | A1 | 4/2009 | Allain et al. |
| 2009/0132054 | A1 | 5/2009 | Zeegers |
| 2009/0222092 | A1 | 9/2009 | Davis et al. |
| 2009/0228108 | A1 | 9/2009 | Keller |
| 2009/0270990 | A1 | 10/2009 | Louis et al. |
| 2010/0049259 | A1 | 2/2010 | Lambrecht et al. |
| 2010/0185289 | A1 | 7/2010 | Kirwan et al. |
| 2010/0204796 | A1 | 8/2010 | Bae et al. |
| 2010/0234958 | A1 | 9/2010 | Linares |
| 2010/0280618 | A1 | 11/2010 | Jodaitis et al. |
| 2011/0098747 | A1 | 4/2011 | Donner et al. |
| 2011/0208311 | A1 | 8/2011 | Janowski |
| 2011/0230971 | A1 | 9/2011 | Donner et al. |
| 2011/0264227 | A1 | 10/2011 | Boyajian et al. |
| 2012/0078371 | A1 | 3/2012 | Gamache et al. |
| 2012/0116466 | A1 | 5/2012 | Dinville et al. |
| 2012/0191196 | A1 | 7/2012 | Louis et al. |
| 2013/0150968 | A1 | 6/2013 | Dinville et al. |
| 2013/0166029 | A1 | 6/2013 | Dinville et al. |

FOREIGN PATENT DOCUMENTS

| | | |
|---|---|---|
| EP | 2113228 | 11/2009 |
| EP | 2327375 | 6/2011 |
| EP | 2340788 | 7/2011 |
| EP | 2363080 | 9/2011 |
| FR | 2747034 | 10/1997 |
| FR | 2827156 | 1/2003 |
| FR | 2846550 | 5/2004 |
| FR | 2861582 | 5/2005 |
| FR | 2879436 | 6/2006 |
| FR | 2880795 | 7/2006 |
| FR | 2891135 | 3/2007 |
| FR | 2897259 | 8/2007 |
| FR | 2916956 | 12/2008 |
| FR | 2987256 | 8/2013 |
| RU | 2004218 | 12/1993 |
| WO | WO 9508306 | 3/1995 |
| WO | WO 9956676 | 11/1999 |
| WO | WO 0024327 | 5/2000 |
| WO | WO 0170141 | 9/2001 |
| WO | WO0213732 | 2/2002 |
| WO | WO 02089701 | 11/2002 |
| WO | WO 03005939 | 1/2003 |
| WO | WO 2004034935 | 4/2004 |
| WO | WO 2004041129 | 5/2004 |
| WO | WO 2004089256 | 10/2004 |
| WO | WO2006047587 | 5/2006 |
| WO | WO 2006120505 | 11/2006 |
| WO | WO 2007078978 | 7/2007 |
| WO | WO 2007093900 | 8/2007 |
| WO | WO2008149223 | 12/2008 |
| WO | WO2009033100 | 3/2009 |
| WO | WO 2010090801 | 8/2010 |

(56) References Cited

FOREIGN PATENT DOCUMENTS

| WO | WO2011080535 | 7/2011 |
|---|---|---|
| WO | WO 2011129973 | 10/2011 |
| WO | WO2013124453 | 8/2013 |

OTHER PUBLICATIONS

World Intellectual Property Organization; International Preliminary Report on Patentability for International App. No. PCT/IB2007/000367, PCT Pub'n No. WO2007093900; Feb. 5, 2008; WIPO; Geneva, Switzerland; all pages.
LDR Medical, by its attorneys; Amendment for Pub'n No. EP2162098, Application No. EP08762820; Jan. 6, 2010; EPO; Munich, Germany; all pages.
European Patent Office; Office Action for Pub'n No. EP2162098, Application No. EP08762820; Jan. 17, 2012; EPO; Munich, Germany; all pages.
LDR Medical, by its attorneys; Reply to Office Action for Pub'n No. EP2162098, Application No. EP08762820; Jul. 27, 2010; EPO; Munich, Germany; all pages.
National Institute of Industrial Property (France); Search Report for Pub'n. No. FR2916956, App. No. FR0704155; Jan. 30, 2008; National Institute of Industrial Property (France); France; all pages.
World Intellectual Property Organization; International Search Report and Written Opinion of the International Searching Authority for International App. No. PCT/IB2008/001484, PCT Pub'n. No. WO2008149223; Feb. 16, 2009; WIPO; Geneva, Switzerland; all pages.
LDR Medical, by its attorneys; Amendment for International App. No. PCT/IB2008/001484, Pub'n. No. WO2008149223; May 13, 2009; WIPO; Geneva, Switzerland; all pages.
World Intellectual Property Organization; International Preliminary Report on Patentability for International App. No. PCT/IB2008/001484, PCT Pub'n. No. WO2008149223; Aug. 5, 2009; WIPO; Geneva, Switzerland; all pages.
World Intellectual Property Organization; International Search Report and Written Opinion of the International Searching Authority for International App. No. WO2011080535, PCT Pub'n. No. PCT/IB2009/008048; Feb. 2, 2011; WIPO; Geneva, Switzerland; all pages.
LDR Medical, by its attorneys; Demand for International App. No. PCT/IB2009/008048, PCT Pub'n. No. WO2011080535; Apr. 19, 2011; WIPO; Geneva, Switzerland; all pages.
World Intellectual Property Organization; Interview Summary for International App. No. PCT/IB2009/008048, PCT Pub'n. No. WO2011080535; Feb. 14, 2012; WIPO; Geneva, Switzerland; all pages.
LDR Medical, by its attorneys; Amendment for International App. No. PCT/IB2009/008048, Pub'n. No. WO2011080535; Apr. 2, 2012; WIPO; Geneva, Switzerland; all pages.
World Intellectual Property Organization; International Preliminary Report on Patentability for International App. No. WO2011080535, PCT Pub'n. No. PCT/IB2009/008048; Apr. 18, 2012; WIPO; Geneva, Switzerland; all pages.
LDR Medical, by its attorneys; Amendment for Pub'n. No. EP2519194, Application No. EP20090812464; May 23, 2013; EPO; Munich, Germany; all pages.
National Institute of Industrial Property (France); Search Report in Fench Pub. No. FR2987256, App. No. FR1251733; Dec. 5, 2012; National Institute of Industrial Property (France); France; all pages.
World Intellectual Property Organization; International Search Report and Written Opinion of the International Searching Authority for International App. No. PCT/EP2013/053622, PCT Pub'n. No. WO2013124453; May 29, 2013; WIPO; Geneva, Switzerland; all pages.
LDR Medical, by its attorneys; Response to International Search Report for International App. No. PCT/EP2013/053622, International Application No. PCT/EP2013/053622; Dec. 18, 2013; WIPO; Geneva, Switzerland; all pages.
World Intellectual Property Organization; International Preliminary Report on Patentability for International App. No. PCT/EP2013/053622, PCT Pub'n. No. WO 2013/124453; Jul. 11, 2014; WIPO; Geneva, Switzerland; all pages.
National Institute of Industrial Property (France); Search Report for Pub'n. No. FR2827156, App. No. FR0109381; Apr. 5, 2002; National Institute of Industrial Property (France); France; all pages.
World Intellectual Property Organization; International Search Report for International App. No. PCT/IB02/03390, PCT Pub'n. No. WO03005939; Mar. 3, 2003; WIPO; Geneva, Switzerland; all pages.
World Intellectual Property Organization; International Preliminary Examination Report for International App. No. PCT/IB02/03390, PCT Pub'n. No. WO03005939; Nov. 6, 2003; WIPO; Geneva, Switzerland; all pages.
European Patent Office; search report in Application No. 10185004, Pub. No. EP2327375; Apr. 6, 2011; European Patent Office; Munich, Germany; All Pages.
European Patent Office; search report in Application No. 13170071, Pub. No. EP2633835; Oct. 1, 2013; European Patent Office; Munich, Germany; All Pages.
National Institute of Industrial Property (France); Preliminary Search Report in Fench Application No. FR0213833, Pub. No. FR2846550; Jul. 10, 2003; National Institute of Industrial Property (France); France; all pages.
World Intellectual Property Organization; International Search Report in International Application No. PCT/IB03/04872, Pub. No. WO2004041129; Mar. 3, 2004; WIPO; Geneva, Switzerland; all pages.
World Intellectual Property Organization; International Preliminary Examination Report for International Application No. PCT/IB03/04872, Pub. No. WO2004041129; Mar. 1, 2005; WIPO; Geneva, Switzerland; all pages.
European Patent Office; Office action and search report in Application No. 05857774, Pub. No. EP1845903; May 6, 2009; European Patent Office; Munich, Germany; All Pages.
LDR Medical, by its attorneys; Amendments and Reply in European Patent Application No. 05857774, Pub. No. EP1845903; Nov. 13, 2009; European Patent Office; Munich, Germany; All Pages.
European Patent Office; Office action and search report in Application No. 05857774, Pub. No. EP1845903; Apr. 11, 2011; European Patent Office; Munich, Germany; All Pages.
LDR Medical, by its attorneys; Amendments and Reply in European Patent Application No. 05857774, Pub. No. EP1845903; Oct. 11, 2011; European Patent Office; Munich, Germany; All Pages.
European Patent Office; Office action and search report in Application No. 11165170, Pub. No. EP2363080; Jul. 21, 2011; European Patent Office; Munich, Germany; All Pages.
LDR Medical, by its attorneys; Amendments and Reply in European Patent Application No. 11165170, Pub. No. EP2363080; Mar. 6, 2012; European Patent Office; Munich, Germany; All Pages.
European Patent Office; Office action in Application No. 11165170, Pub. No. EP2363080; May 15, 2012; European Patent Office; Munich, Germany; All Pages.
National Institute of Industrial Property (France); Search Report for Pub'n. No. FR2879436, App. No. FR0413728; Aug. 11, 2005; National Institute of Industrial Property (France); France; all pages.
World Intellectual Property Organization; International Search Report and Written Opinon of the International Searching Authority for PCT Pub'n. No. WO2006120505, App. No. PCT/IB2005/004093; Aug. 31, 2006; WIPO; Geneva, Switzerland; all pages.
LDR Medical, by its attorneys; Chapter II amendments for PCT Pub'n. No. WO2006120505, App. No. PCT/IB2005/004093; Oct. 30, 2006; WIPO; Geneva, Switzerland; All Pages.
World Intellectual Property Organization; International Preliminary Report on Patentability for PCT Pub'n. No. WO2006120505, App. No. PCT/IB2005/004093; Feb. 22, 2007; WIPO; Geneva, Switzerland; all pages.
National Institute of Industrial Property (France); Preliminary Search Report in French Pub. No. FR2891135, App'n. No. FR0509740; Jun. 27, 2006; National Institute of Industrial Property (France); France; all pages.

(56) References Cited

OTHER PUBLICATIONS

World Intellectual Property Organization; International Search Report for PCT Pub'n. No. WO2007034310, App'n. No. PCT/IP/006/02632; Feb. 13, 2007; WIPO; Geneva, Switzerland; all pages.
World Intellectual Property Organization; Written Opinion of the International Searching Authority for PCT Pub'n No. WO2007034310, App'n No PCT/IP/006/02632; Feb. 13, 2007; WIPO; Geneva, Switzerland; all pages.
World Intellectual Property Organization; International Preliminary Report on Patentability for PCT Pub'n No. WO2007034310, App'n No PCT/IP/006/02632; Aug. 14, 2007; WIPO; Geneva, Switzerland; all pages.
LDR Medical, by its attorneys; Amendment for Pub'n No. EP1996127, Application No. EP7733892; Nov. 26, 2008; EPO; Munich, Germany; all pages.
National Institute of Industrial Property (France); Search Report for Pub'n. No. FR2897259, App. No. FR0601315; Oct. 11, 2006; National Institute of Industrial Property (France); France; all pages.
National Institute of Industrial Property (France); Search Report in Fench Pub. No. FR3005569, App. No. FR1354421; Feb. 12, 2014; National Institute of Industrial Property (France); France; all pages.
World Intellectual Property Organization; International Search Report for International App. No. WO2014184367, PCT Pub'n. No. PCT/EP2014/060135; Aug. 26, 2014; WIPO; Geneva, Switzerland; all pages.
National Institute of Industrial Property (France); Search Report in Fench Pub. No. FR3016793, App. No. FR1450749; Sep. 11, 2014; National Institute of Industrial Property (France); France; all pages.
World Intellectual Property Organization; International Search Report and Written Opinion of the International Searching Authority for International App. No. WO2015114122, PCT Pub'n. No. PCT/EP2015/052019; May 13, 2015; WIPO; Geneva, Switzerland; all pages.
European Patent Office; Office Action for App. No. 02784881, Pub'n. No. EP1406563; Mar. 13, 2009; EPO; Munich, Germany; all pages.
LDR Medical, by its attorneys; Reply to Office Action for App. No. 02784881, Pub'n. No. EP1406563; Jul. 22, 2009; EPO; Munich, Germany; all pages.
European Patent Office; Office Action for App. No. 02784881, Pub'n. No. EP1406563; Aug. 4, 2009; EPO; Munich, Germany; all pages.
LDR Medical, by its attorneys; Reply to Office Action for App. No. 02784881, Pub'n. No. EP1406563; Oct. 14, 2009; EPO; Munich, Germany; all pages.
European Patent Office; Notice of Intent to Grant Patent for App. No. 02784881, Pub'n No. EP1406563; Aug. 26, 2010; EPO; Munich, Germany; all pages.
European Patent Office; Search Report for Pub'n. No. EP2113228, Application No. EP09009533; Oct. 6, 2009; EPO; Munich, Germany; all pages.
LDR Medical, by its attorneys; Amendment for Pub'n. No. EP2113228, Application No. EP09009533; Apr. 26, 2010; EPO; Munich, Germany; all pages.
European Patent Office; Search Report for Pub'n. No. EP2340788, Application No. EP11157596; Jun. 8, 2011; EPO; Munich, Germany; all pages.

* cited by examiner

INSTRUMENTS AND METHODS FOR REMOVING FIXATION DEVICES FROM INTERVERTEBRAL IMPLANTS

CROSS-REFERENCE TO RELATED APPLICATIONS

This application is a continuation in part of International Application No. PCT/IB2009/008048 filed Dec. 31, 2009, in accordance with the Patent Cooperation Treaty. International Application No. PCT/IB2009/008048 is incorporated herein by reference.

BACKGROUND

This disclosure concerns orthopedic implants, including spinal implants such as intervertebral prostheses and intersomatic cages, for example. In particular, this disclosure is directed to devices and methods for removing fixation devices, such as anchors, pins, staples, screws, nails, etc., that have been used to affix an intervertebral implant to one or more adjacent spinal elements.

A healthy intervertebral disc is flexible enough to allow movement between a vertebra and another adjacent spinal column element, such as another vertebra, the coccyx, or the sacrum. This movement accommodates bending of the spine. Disease, degeneration, or injury of the tissues of a natural intervertebral disc often leads to intense pain and reduced spinal mobility. When disease, degeneration, or injury of the natural intervertebral disc has progressed to the point where non-operative care such as medication, injections, and/or physical therapy is ineffective, surgical intervention may be required.

A common procedure for treatment of diseased, degenerated, or injured intervertebral discs involves removal of the natural tissues of the disc and fusion of the adjacent vertebrae. Although fusion eliminates the mobility between the adjacent vertebrae, often it is the preferred method of treatment of disc degeneration or injury.

Intervertebral disc prostheses have been developed to treat diseased, degenerated, or injured intervertebral discs and still provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from postoperative immobilization instrumentation that may be present in fusion procedures.

One problem in this field concerns the stability of spinal implants in the disc space once they have been implanted. For example, there is a risk that the implant will shift in the intervertebral space due to forces imposed when the patient moves, even when the implant is provided with notches or teeth on its vertebral contact surfaces. Therefore, it is often necessary to affix the spinal implant to the adjacent vertebrae during implantation. A number of solutions are known to affix the spinal implant to the adjacent vertebrae using a bone anchoring device, such as an anchor, pin, nail, screw, staple, and other mechanical fixation structures. International Application No. PCT/IB2009/008048 filed Dec. 31, 2009, by the assignee of the present application describes various particularly advantageous fixation devices, instruments, and methods.

Access to the intervertebral spaces often is particularly delicate due to the dimensions involved and the presence of blood vessels and nerves in the approach to the intervertebral space. Bone anchoring devices should have sufficient size, strength, and positioning to ensure good fixation, but preferably the configuration of the anchoring devices, installation tools, and fixation methods allows fixation of the implant without endangering the surrounding blood vessels and nerves. International Application No. PCT/IB2009/008048, for example, describes various advantageous devices, instruments, and methods that reduce the space required in the approach to the intervertebral location compared to conventional devices and methods.

In an ideal outcome, the placement an intervertebral implant will be permanent, and withdrawal of the implant or modification of its position never will be needed. In practice, though, circumstance can arise which indicate that an intervertebral implant should be removed or reposition following the initial fixation to the adjacent vertebral structures. This disclosure describes various structures and steps that may be useful for removing or repositioning an implant after its initial fixation.

SUMMARY OF THE DISCLOSURE

Various embodiments of anchor removal instruments and methods for using the instruments are described. In some embodiments, an intervertebral implant anchor extractor tool comprises a support, a support retainer configured to hold the support fixed with respect to the implant, an extractor having an anchor retainer, and an extractor guide. An embodiment of a method of using this implant anchor extractor tool comprises the steps of obtaining access to an anchor, grasping the anchor, and applying a withdrawal force on the anchor while applying a countervailing force against the implant or a vertebral structure.

DETAILED DESCRIPTION OF VARIOUS EMBODIMENTS

Figure 1:
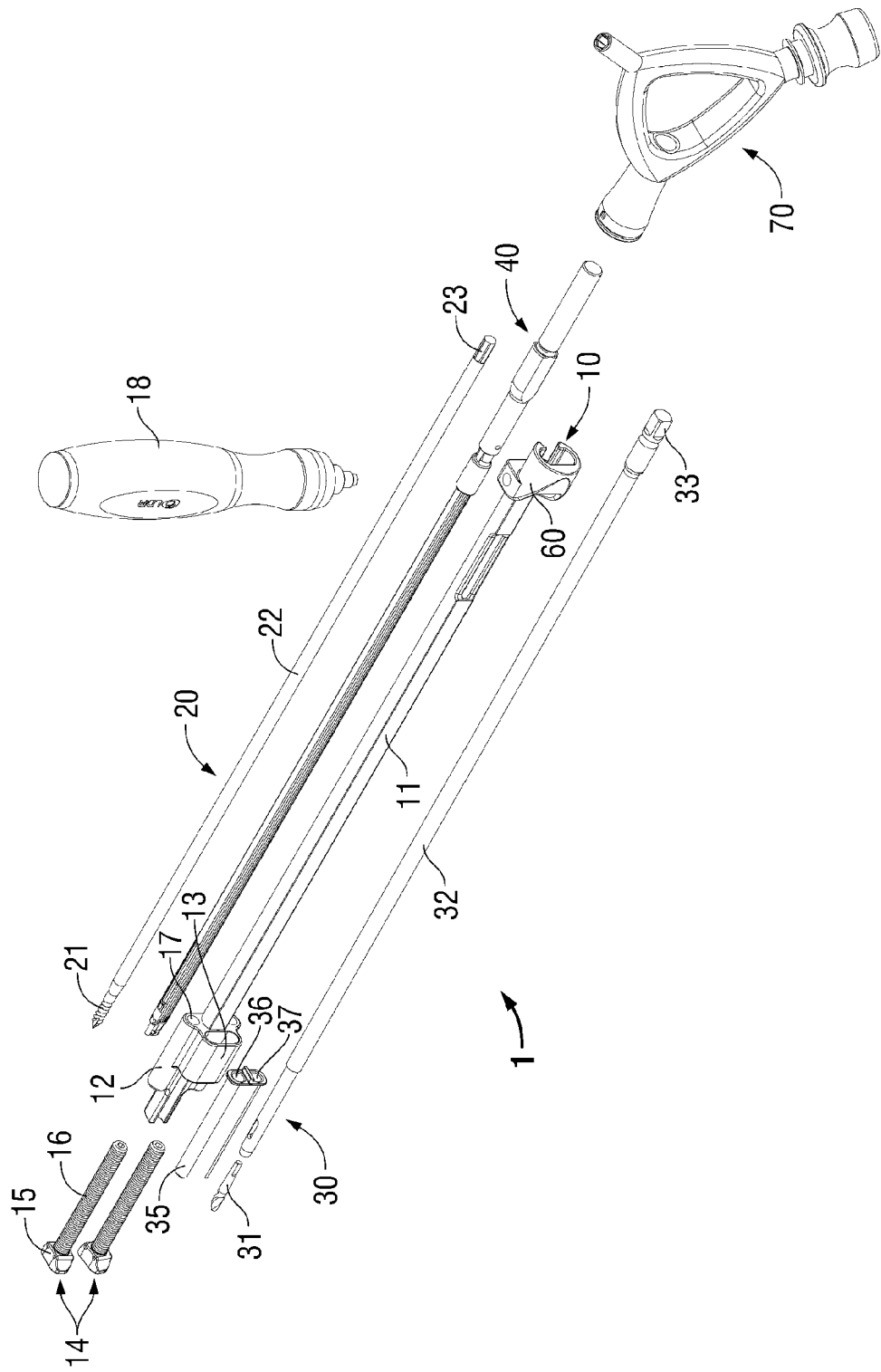
FIG. 1 depicts various components of an embodiment of an anchor removal instrument.
Figure 14:
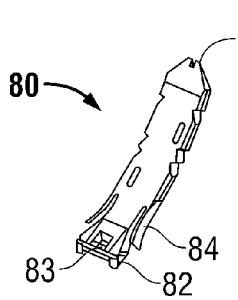
FIGS. 14 and 15 depict an embodiment of an anchor for an implant.
Figure 15:
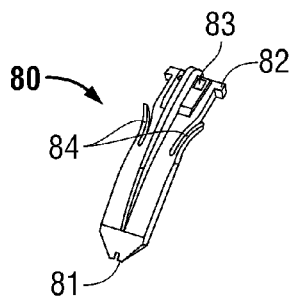

FIG. 1 depicts one of many possible embodiment of an instrument (1) for removing fixation devices of intervertebral implants. The example shown in FIG. 1 is implemented with features particularly useful for extracting a plate-like anchor, for example as depicted in FIGS. 14 and 15, but other instrument embodiments can be implemented with features useful for extracting other types of anchors or for fixation structures such as pins, nails, screws, staples, etc.

The embodiment of instrument (1) illustrated in FIG. 1 comprises a support (10), a support retainer or coupler (20), a drill assembly (30), a drill guide (35), an extractor (40), an extractor support (60), and an operation handle (70). In this embodiment, the support assembly (10) is configured with support and stabilization handle (18), and as depicted for example in FIG. 2, with support tube (11), support head (12), and extractor support (60). Support head (12) and/or extractor support (60) can be separate components, or made integral with support assembly (10). FIG. 3 depicts further detail of support head (12) of this embodiment, showing a drill guide support made integral with an extractor guide (in structure 13).

The embodiment of FIG. 3 is configured with a separate support head (12) attached to support tube (11), which can be accomplished with conventional structures such as threads, pins, screws, adhesives, solder, etc. Support head (12), however, could be integral with tube (11) in other embodiments. Support head (12) in this embodiment has drill guide support and extractor guide (13) configured as an oblong channel surrounded by a hood, but the drill guide support and extractor guide may also be deployed as separate elements at other locations of instrument (1), for example as various configurations of channels, eyes, loops, hooks, hoods, brackets, etc. The illustrated embodiment of support head (12) also provides for attachment of separate contact surfaces to maintain the support head (12) at a particular distance from the vertebrae or the implant, but similar contact surfaces in other embodiments may be made integral with head (12). In this example, contact surfaces are deployed with depth stops (14) that are devised as bumpers (15) with the contact faces, and bumpers (15) are supported on bumper supports (16) configured as threaded rods. Head (12) in this embodiment has contact surface supports 17 configured as threaded drillings in head (12). Threaded rods (16) engage the threaded drillings (17) in this embodiment, thus allowing for the distance between the contact surfaces of bumpers (15) and the support head (12) to be adjusted by screwing rods (12). In the illustrated embodiment of FIG. 1, the contact surfaces of depth stops (14) are configured to abut the respective adjacent vertebrae, but in other embodiments one or more contact surfaces may be deployed, and one or more (or all) of the contact surfaces may optionally be configured to abut the implant instead of a vertebra.

In various embodiments, a coupler or retainer may be configured to fix the support assembly (10) to the implant or otherwise retain the support assembly (10) fixed with respect to the implant. For the embodiments illustrated in FIGS. 1-3, support tube (11) is configured with a channel extending the length of tube (11), through which attachment screw (20) can pass. Attachment screw (20) in this example comprises screw tip (21), screw shaft (22), and screw drive adapter (23). In the embodiment illustrated in FIG. 1, screw tip (21) is deployed with self tapping threads. Rotation of this attachment screw (20) with tip (21) engaged in the implant, for example a hole deployed on an exposed surface of the implant, will cause the threads of tip (21) to engage the implant. In this way, a shoulder or similar blocking structure of shaft (22) can be drawn to abut a corresponding blocking structure in shaft (11) or head (12), causing support assembly (10) to be fixed to the implant or at least be held fixed with respect to the implant. Alternative to self-tapping threads on tip (21) include machine threads, interrupted threads, tapered threads, locking lugs, pins, and other structures that can mate with corresponding structures of the implant to hold the support assembly (10).

The illustrated embodiment uses a hex-headed screw drive adapter (23) connected to the tip (21) by shaft (22), but other configurations to actuate the coupling or retaining structures can be used. For example, the coupling or retaining structures could be actuated by a reciprocating rod that, in an activated position, causes lugs or other locking means to move into engagement with corresponding latching structures of the implant, and in an inactivated position, causes the lugs or other locking means to retract from the corresponding latching structures of the implant.

In some implant embodiments, access to the anchoring device may be obscured by part of the implant. For these types of implants, the anchor removal instrument may be deployed with means to expose a portion of the anchoring device so that the anchoring device can be grasped by an extractor. Such means may provide access to the anchoring device, for example, by opening, separating, moving, or removing portions of the implant. In the embodiment of an anchor removal instrument (1) depicted in FIG. 1, for example, a drill assembly (30) is provided to drill access holes in the implant through which the anchors can be grasped. This embodiment of drill assembly (30) comprises a drill bit (31), which may be deployed in any format appropriate for the implant material, including a spade, brad point, or twist bit, a hole saw, or an end mill. Drill bit (31) also may be deployed as a hollow shaft Forstner bit driven by a hollow drill shaft (32), which would allow the application of suction through the shafts to the drilling site to draw away chips and other debris from the drilling operation.

FIG. 3 also depicts an embodiment of a drill guide (35) used to support drill assembly (30) and direct drill bit (31) to an appropriate location on the implant when drilling the implant to gain access to the anchors. This embodiment of drill guide (35) may be implemented in various materials, such as steel, aluminum, titanium, plastic, etc. The illustrated embodiment is deployed as an elongated bar with rounded corners having a profile that complements the profile of a channel in the drill guide support and extractor guide (13). This embodiment also has upper guide (36) and lower guide (37), which are provided by borings along the length of the body of guide (35). Preferably, the illustrated embodiment is arranged so that when support assembly (10) is fixed to the implant using attachment screw (20), upper guide (36) and lower guide (37) are located to directly guide drill bit (31) to the respective locations of the implant appropriate to gain access to the anchors and to hold drill bit (31) in that location during the drilling operation.

Drill guide (35) can be inserted in or removed from drill guide support (13) in the embodiment illustrated in FIGS. 1 and 3. When drill guide (35) is removed in this embodiment, structure (13) may also be used as an extractor guide, as discussed further below. Accordingly, this example of drill guide (35) also has extraction tab (38), which may be used to extract the drill guide (35) from the drill guide support (13), for example by grasping tab (38) with forceps.

Figure 2:
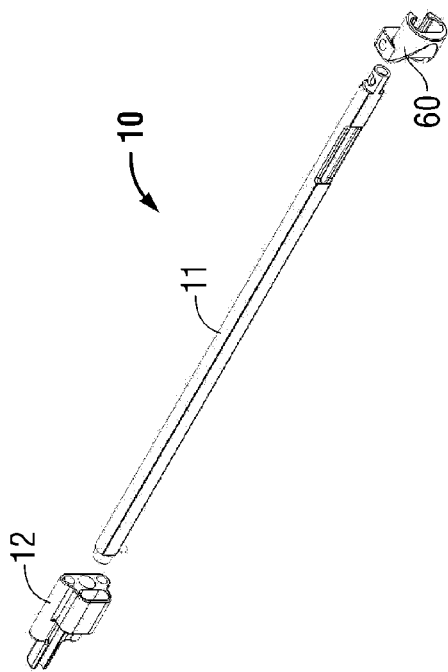
FIG. 2 depicts various components of an embodiment of a support assembly for the device of FIG. 1.
Figure 3:
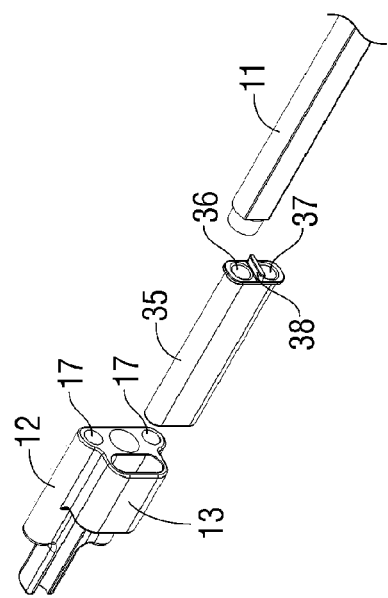
FIG. 3 depicts further details of the components depicted in FIG. 2.
Figure 5:
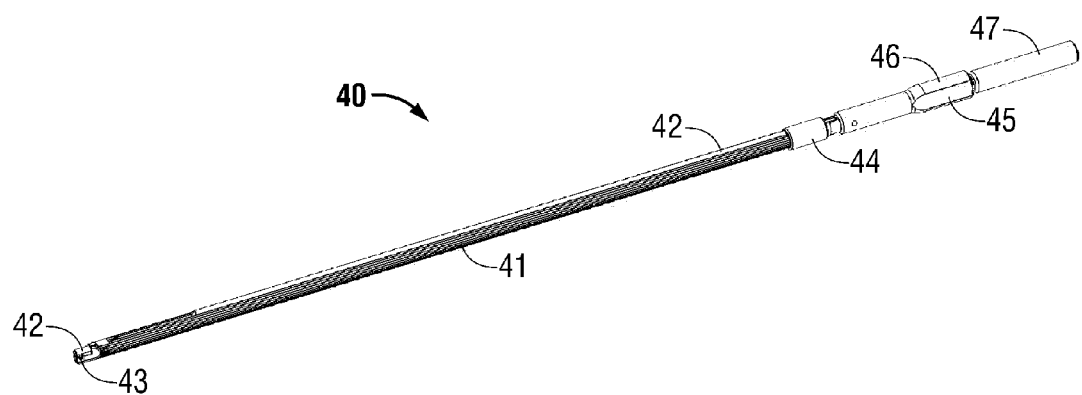
FIG. 5 depicts the extractor assembly of the instrument depicted in FIG. 1.

In the embodiments illustrated in FIGS. 1-3 are supported with respect to the implant by attachment screw (20) and ends the anchors fixing the implant to the vertebrae have been exposed using drill assembly (30) and drill guide (35), the equipment usually will be ready to extract the anchors. For many types of embodiments, an extra assembly similar to the embodiment shown in FIG. 5 will be appropriate for extracting the anchors. The extractor assembly (40) embodiment illustrated in FIG. 5 comprises extractor shaft (41), anchor attachment rod (42), attachment hook (43), and anchor attachment rod control (44).

Figure 6:
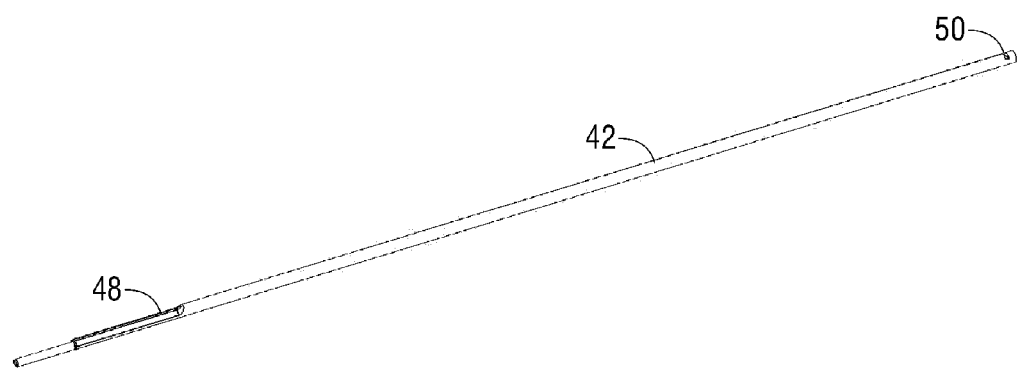
FIG. 6 depicts the anchor attachment rod of the extractor assembly depicted in FIG. 5.
Figure 7:
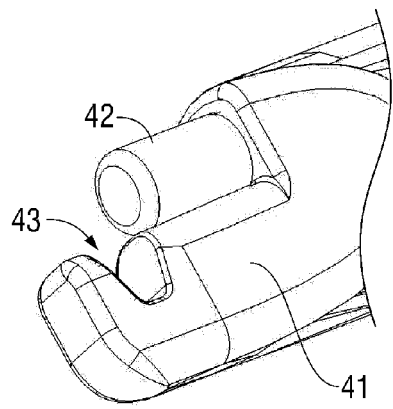
FIGS. 7 and 8 depict various components of the extractor assembly depicted in FIG. 5, with the anchor attachment rod in an open position in FIG. 7 and a closed position in FIG. 8.
Figure 8:
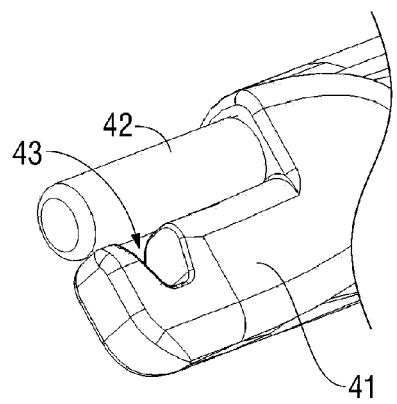
Figure 9:
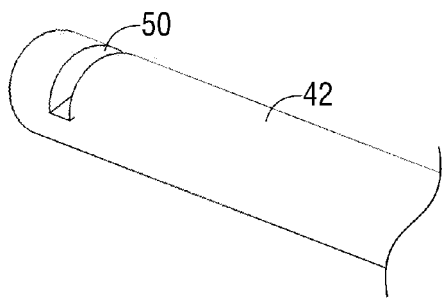
FIG. 9 depicts the structure of an end of the anchor attachment rod depicted in FIG. 6.
Figure 10:
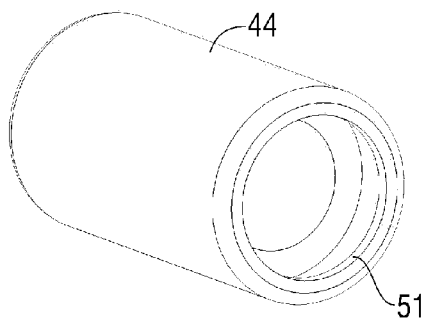
FIG. 10 depicts the anchor attachment rod control of the extractor assembly depicted in FIG. 5.
Figure 11:
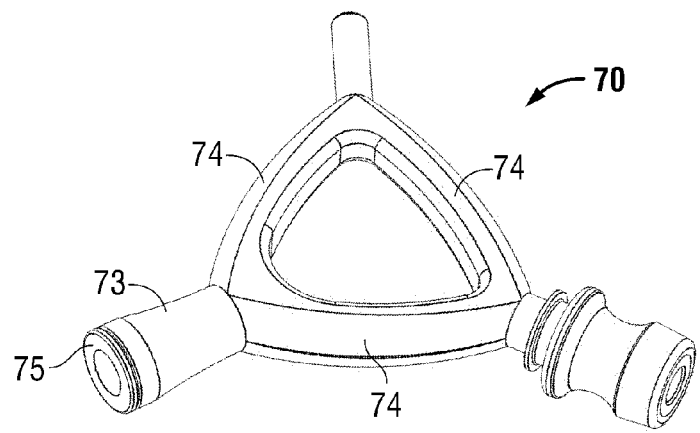
FIGS. 11-13 depict an operating handle for the extractor assembly depicted in FIG. 5.
Figure 12:
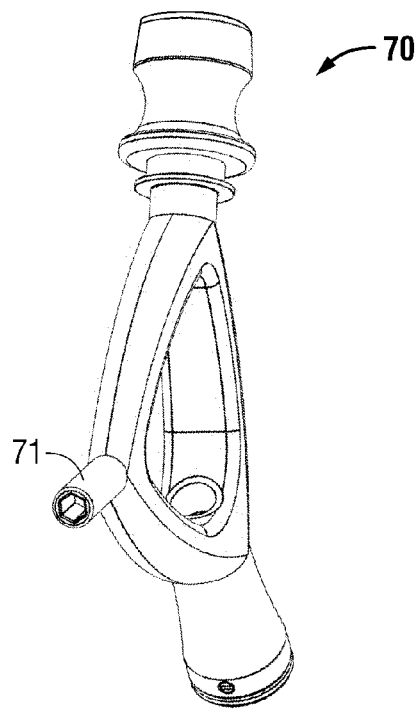
Figure 13:
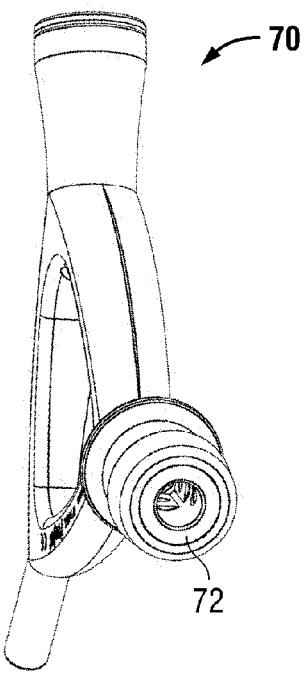

For the embodiment shown in FIGS. 5-10, anchor attachment rod (42) reciprocates in a channel disposed along a longitudinal edge of extractor shaft (41). The channel in this embodiment terminates near the hook end of shaft (41) in a bore disposed through the body of shaft (41). The end of rod (42) in this embodiment passes through the bore and may reciprocate in the bore, and the shaft material surrounding the bore retains the rod (42) against the shaft (41). For this embodiment, the hook end of rod (42) is cylindrically shaped and sized to pass smoothly through the bore near the end of shaft (41), and the exterior facing surface of rod (42) near this end is recessed (48) to reduce the profile of extractor assembly (40) to provide extra clearance in the surgical opening. Near the other end of rod (42) in this embodiment, a notch (50) is disposed as shown in FIGS. 6 and 9. This notch receives rim (50) disposed circumferentially around the interior bore of a cylindrically shaped anchor attachment rod control (44). In this embodiment, control (44) is deployed with interior threads that engage exterior threads along shaft (41), with rotation of control (44) causing it to move along the longitudinal axis of shaft (41). This longitudinal movement of control (44) causes rod (42) to move linearly along the longitudinal axis of shaft (41), due to the engagement of rim (51) in notch (50).

The linear movement of rod (42) along the side of shaft (41) in the illustrated embodiments opens and closes attachment hook (43) disposed at an end of shaft (41), for example as depicted in FIGS. 7 and 8, to function as an anchor attachment or retainer. When the hook (43) is open as shown in FIG. 7, a grasping structure on an anchor can be placed in the open area of the hook. When the hook (43) is closed as shown in FIG. 8, the anchor is locked to shaft (41) by rod (42) as shown, for example, in FIGS. 41 and 44-48.

Figure 4:
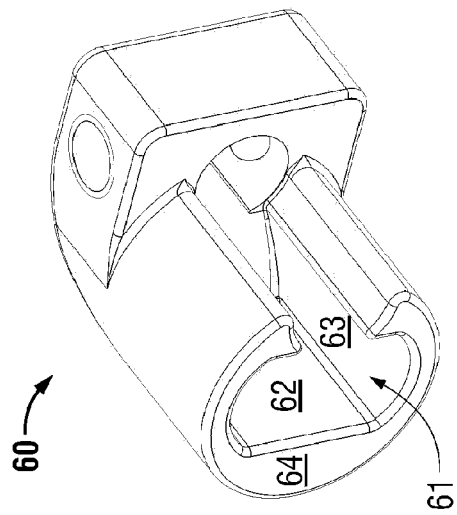
FIG. 4 depicts the extractor support/guide of the instrument depicted in FIGS. 1 and 2.

In the illustrated embodiments, the extractor assembly (40) may be supported at the end opposite hook (43) by an extractor support (60). Extractor support (60) is a removable structure in these embodiments, but other embodiments may have support (60) integrally formed with support assembly (10) or permanently or semi-permanently attached to support assembly (10). For the embodiment depicted in FIG. 4, extractor support (60) comprises an extractor guide channel (61), a flat channel surface (62), a pair of curved channel surfaces (63), and a bearing surface (64). In these embodiments, to put the extractor assembly (40) in place to extract an anchor, the hook end of extractor assembly (40) first is inserted through channel 61 and then through extractor guide (13). Then, this extractor assembly (40) is further pushed toward the implant until the flat channel engagement surface (45) of shaft (41) is adjacent to flat channel surface (62) of channel (61), and the curved channel engagement surfaces (46) of shaft (41) are respectively adjacent to curved channel surfaces (63) of channel (61). In this way, extractor assembly (40) has an appropriately limited range of linear movement in which the cooperation of the curved and flat surfaces of the respective components of shaft (41) and support (60) inhibit rotation of shaft (41); thus, support (60) serves also as an extractor guide. In this limited range, a withdrawing force can be transmitted to the anchor far enough to extract it from the implant without shaft (41) rotating. In these embodiments, this configuration allows the anchor withdrawing force to originate by rotating a threaded handle, such as the examples illustrated in FIGS. 11-13 and 42-43, on mating threads of attachment adapter (47). This rotation of handle (70) causes shaft (41) to move linearly away from the implant, causing the anchor attachment/retainer (e.g., hook 43 and tip of rod 42) to exert the withdrawing force on the anchor. For withdrawal of curved anchors, for example as illustrated in FIGS. 41 and 44-46, the oblong shape of the channel in extractor guide (13) allows the hook end of shaft (41) to rise and fall in the channel, thus accommodating the curved path the anchor follows in its extraction from the implant.

An extraction actuator may take forms other than the illustrated handles (70). For example, linear or rotational ratchet assemblies may be useful in some situations, and in some situations with particularly firmly seated anchors, a slide hammer configuration may be indicated. In many routine situations, though, an actuator such as the illustrated handles (70) will be preferred. The handle (70) embodiment illustrated in FIGS. 11-14 has an extraction adapter (73) configured to engage attachment adapter (47) of extractor shaft (41) for extraction of an anchor. For example, threads in adapter (73) may engage corresponding threads on adapter (47). In this example, shaft (41) is inserted in support/guide (60) as far as needed to attach to the anchor and retain the anchor to the shaft (41). Then, handle (70) is rotated to thread it onto adapter (47) using adapter (73), until bearing surface (75) of adapter (73) abuts bearing surface (64) of extractor support/guide (60). At this point, further rotation of handle (70) causes shaft (41) to move linearly away from the implant, thus extracting the anchor from the implant.

The actuation handle (70) embodiment illustrated in FIGS. 1 and 11-13 provides other features, too. For example, hex drive adapter (71) is configured to mate with screw drive adapter (23), allowing handle (70) to be used to drive screw shaft (22). This embodiment also provides square drive adapter (72) configured to mate with drill drive adapter (33) allowing the handle to rotate shaft (32). Such hand powered drilling may be sufficient in many situations, but some embodiments may instead use a power drive for drill assembly (30). Any of these types of adapters may be deployed with locking mechanisms for mating adapters, and may have quick-release configurations for such mechanisms. For example, when a collar is in a first "hold" position, a ball detent in adapter (72) could firmly hold drive adapter (33) in adapter (72), and when the collar is in a second "released" position, pressure on the ball detent would be removed and drive adapter (33) released.

The embodiment shown in FIG. 1 is particularly adapted for use with curved-plate type anchors, such as those described in International Application No. PCT/IB2009/008048. Other embodiments, however, may be adapted for other types of anchors (straight and curved) and retaining structures, e.g., pins, staples, screws, nails, etc. FIGS. 14-20 depict examples of anchors for which the embodiment shown in FIG. 1 is particularly useful. The anchor (80) embodiment illustrated in FIGS. 14-19 has is generally curved along its length, with an insertion tip (81) configured for insertion in a vertebral structure at one end and a retainer (82) at the other end, which prevents over-insertion of the anchor in the implant (90). These embodiments also have latches (84), which hold the anchor (80) in the implant (90) after full insertion of the anchor, and a withdrawal opening (83). This withdrawal opening (83) comprises an open area through the anchor (80), allowing grasping of the anchor.

Figure 16:
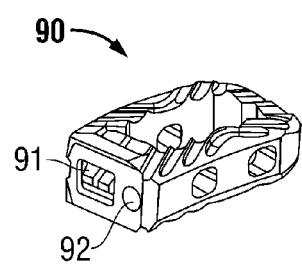
FIG. 16 depicts an implant configured for use of the anchor depicted in FIGS. 14 and 15.
Figure 17:
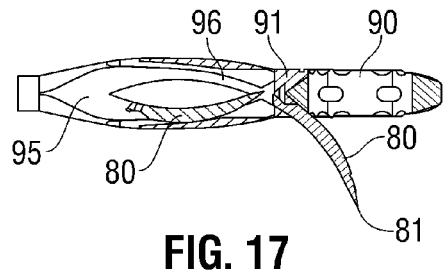
FIGS. 17-18 and depict an insertion instrument used to place an implant and deliver anchors through the implant into adjacent vertebrae.
Figure 18:
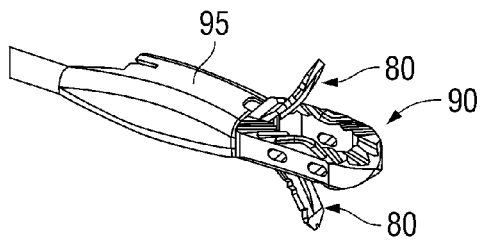
Figure 19:
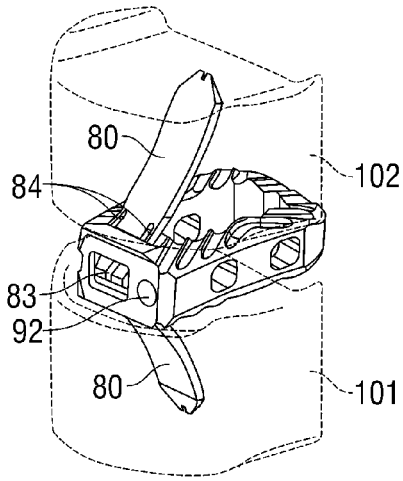
FIG. 19 depicts the anchor of FIGS. 14-15 and the implant of FIG. 16 implanted between two vertebrae.
Figure 20:
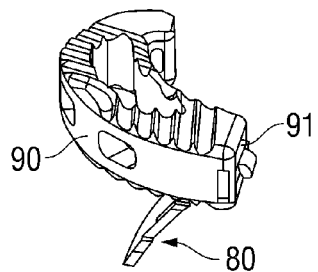
FIG. 20 depicts an embodiment of an implant and anchor combination suitable for transforaminal lumbar interbody fusion.

FIGS. 16-19 depict an embodiment of an implant (90) useful with the anchor (80) embodiment illustrated in FIGS. 14 and 15, and with other types of anchors as well. This embodiment has an attachment hole (92), which is useful both during implantation of the implant and for retaining the anchor removal instrument (1) during any extraction of an anchor. For example, using the attachment screw (20) embodiment of FIG. 1, screw tip (21) can be turned into attachment hole (92) causing support assembly (10) to be fixed to the implant or at least be held fixed with respect to the implant. The embodiment depicted in FIGS. 16-19 also comprise anchor guide slots (91), which allow anchor (80) to be inserted into implant (90) and driven into an adjacent vertebra through a surgical approach in surrounding tissue that need only be large enough to pass the implant (80). An embodiment of an insertion head (95) that facilitates this minimally invasive approach is depicted in FIGS. 17 and 18, showing anchor insertion channels (96) that are used to guide the anchor (80) along its arc-shaped route into the implant (80) and then an adjacent vertebra. FIG. 19 shows the use of these embodiments in an implantation of implant (90) between two vertebrae, illustrating the insertion of anchors (80) into those vertebrae. FIG. 20 shows an implant (90) embodiment useful for transforaminal lumbar interbody fusion, using a single anchor (80), but the general structures and steps applicable to the embodiments of FIGS. 14-19 are also applicable to this arrangement. FIGS. 16 and 20 show examples of implants for which an anchor removal instrument may be useful, but appropriately configured anchor removal instruments may be useful for other implants (including intervertebral prostheses and intersomatic cages) that use one or more anchors or other retaining structures.

FIGS. 21-49 depict an example of anchor withdrawal using embodiments of anchor removal instrument (1) previously described. The following discussions are directed to those particular embodiments, but are not restrictive as to other embodiments of structures or methods.

Figure 23:
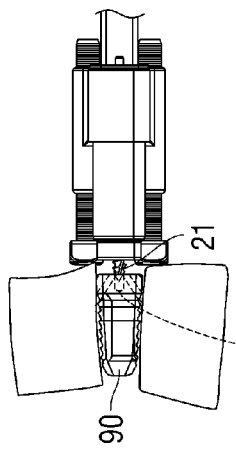
FIGS. 21-49 depict a method of using the embodiments depicted in FIGS. 1-13.
Figure 24:
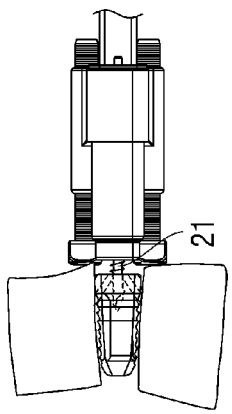
Figure 25:
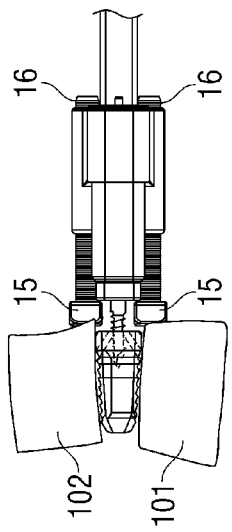
Figure 21:
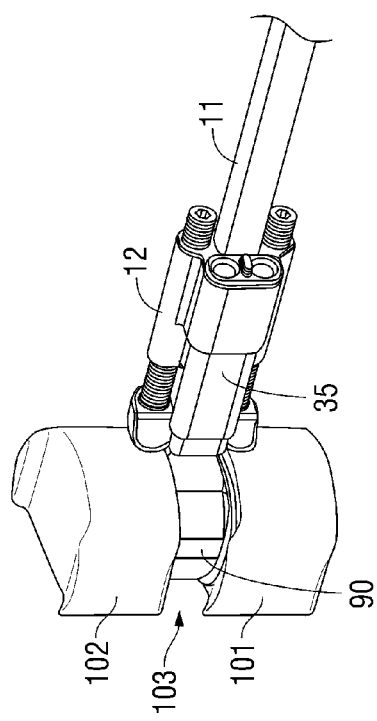
Figure 22:
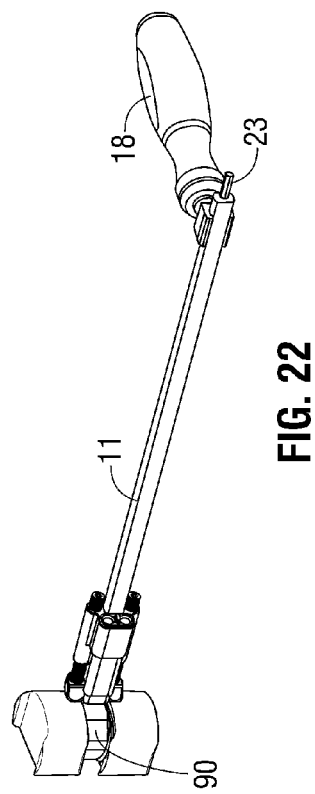

FIG. 21 depicts initial placement of an anchor removal instrument (1) near an implanted implant (90) after the surgical approach to the intervertebral space is obtained. It is convenient to make initial placement of support head (12) with drill guide (35) in place in the drill guide support (13). Attachment screw (20) may already be inserted partially in the channel of support tube (11), or may be inserted following initial placement of the head (12). With the attachment screw (20) in place as shown in FIG. 22, it is screwed in the implant (90), preferably into an attachment hole (92) in the implant, as shown in FIGS. 23-24. Drilling force is applied at screw drive adapter (23), either with a hand drive (for example, with handle (70) shown in FIGS. 11-13) or a power drive. The operative distance of head (12) from the vertebrae (101, 102) is set by adjusting bumper supports (16) in depth stop attachment holes (17) in support head (12), causing bumpers (15) to abut the respective vertebrae (101, 102) as shown in FIG. 25. Alternatively, if the circumstance allow (e.g., by providing sufficient working space), one or more bumpers (15) may be adjusted to abut the implant (90) instead of the vertebrae, or head (12) may itself directly abut the implant or one or more vertebrae. Regardless of the abutment configuration, a countervailing force preferably acts directly on the implant or a vertebra to counteract the extraction force exerted on the anchor during its extraction.

Figure 26:
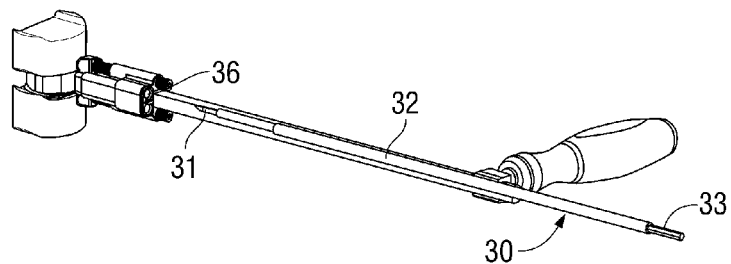
Figure 27:
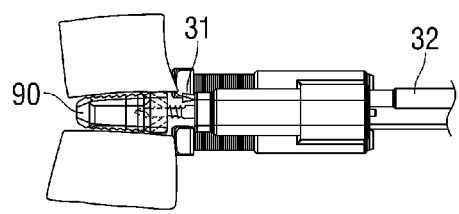
Figure 28:
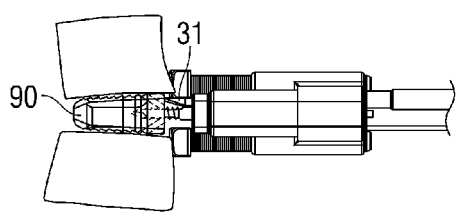
Figure 29:
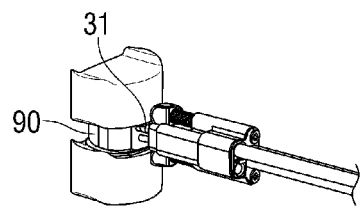
Figure 30:
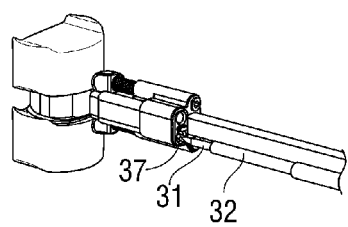
Figure 31:
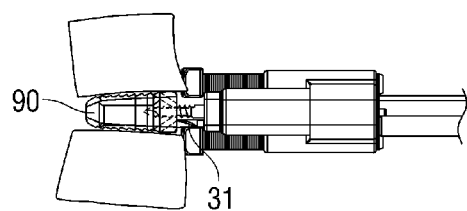

FIGS. 26-29 depict an example of steps that can be used to gain access to an anchor for grasping it. For example, drill assembly (30) is put in place to drill a hole in implant (90) to expose withdrawal opening (83) of a first anchor (80). FIG. 26 shows bit (31) approaching the outer opening of upper guide (36). FIG. 27 shows bit (31) emerging from the inner opening of upper guide (36). FIGS. 28 and 29 show bit (31) engaging implant (90) in the drilling operation. Following this drilling operation, withdrawal opening (83) of the first anchor (80) is exposed and can be grasped with hook (43) of extractor assembly (40). FIGS. 30 and 31 depict the use of lower guide (37) to direct and stabilize drill assembly (30) while drill bit (31) creates another opening in implant 90 to expose withdrawal opening (83) of a second anchor (80). Preferably, support assembly (10) is configured so that engagement of screw tip (21) into attachment hole (92) of the implant automatically aligns upper guide (36) and lower guide (37) in proper position for drilling optimally located holes in implant (90) to gain optimal access to the withdrawal openings (83) of the anchors (80).

Figure 32:
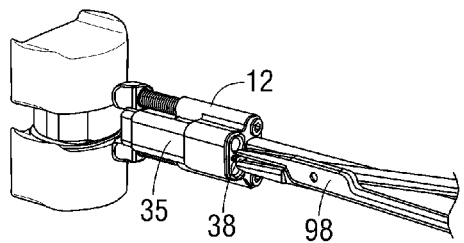
Figure 33:
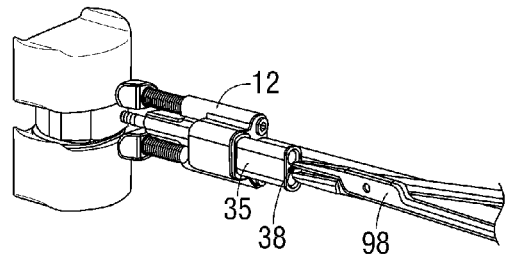

Once the access to withdrawal openings (83) of the anchors (80) is obtained, drill guide (35) can be removed from drill guide support (13). FIGS. 32 and 33 show forceps (98) being used to grasp extraction tab (38) on drill guide (35) and pull the tab (38) to withdraw the guide (35) from the support (13).

Figure 34:
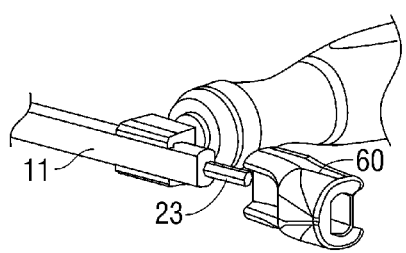
Figure 35:
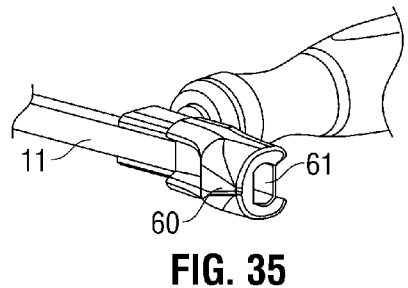

FIGS. 34 and 35 depict extractor support/guide (60) being placed on support tube (11). Other embodiments that use an extractor support/guide, however, may have the support/guide (60) permanently attached or made integral with tube (11) or another structure of instrument (1).

Figure 36:
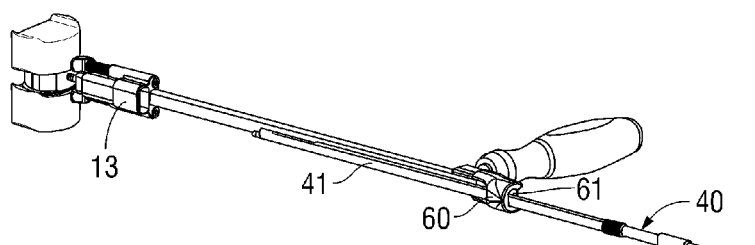
Figure 37:
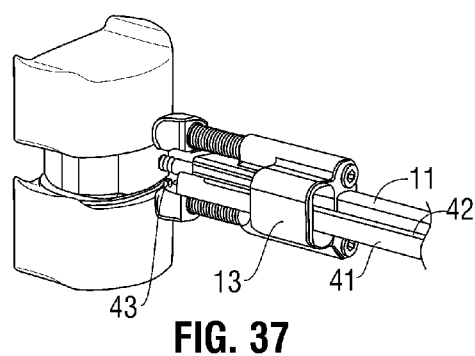
Figure 38:
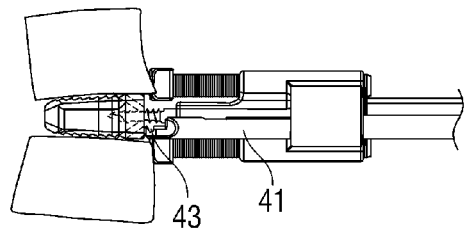
Figure 39:
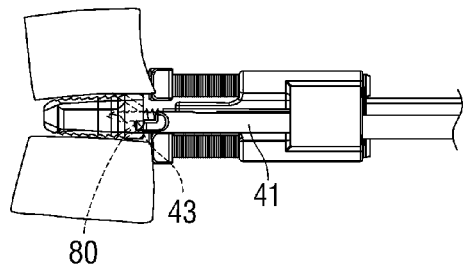
Figure 40:
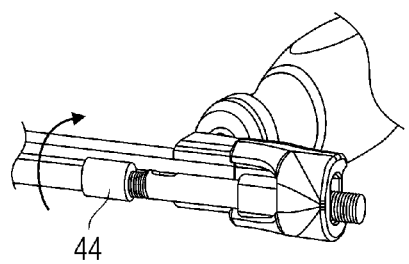
Figure 41:
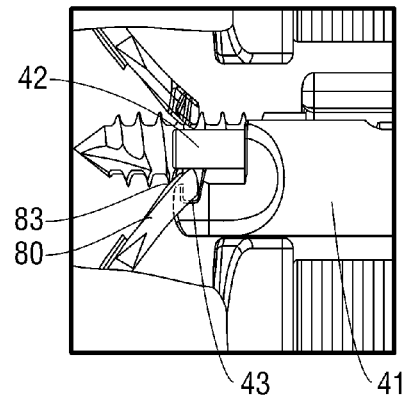

FIGS. 36 and 37 depict the placement of extractor assembly (40). In this example, attachment hook (43) is inserted through extractor guide channel (61) of extractor support/guide (60) and through the oblong channel of extractor guide (13). As shown in FIGS. 37-39, anchor attachment rod (42) is retracted to leave attachment hook (43) open to grasp the end of anchor (80) using withdrawal opening (83) of the anchor. With the rear of anchor (80) in place in the notch of attachment hook (43), anchor attachment rod control (44) is rotated to urge anchor attachment rod (42) forward to close attachment hook (43), as shown for example in FIGS. 40 and 41. Anchor (80) is now securely attached to and retained by extractor assembly (40).

Figure 42:
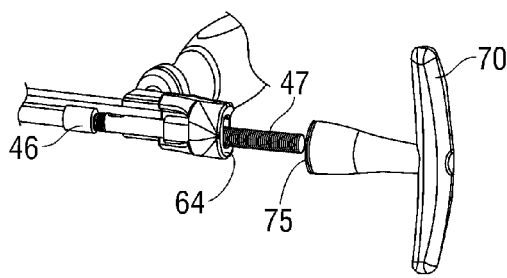
Figure 43:
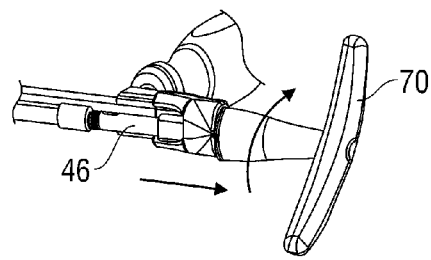
Figure 44:
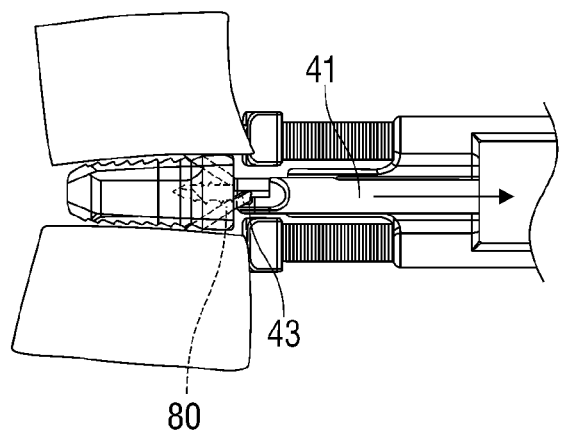
Figure 45:
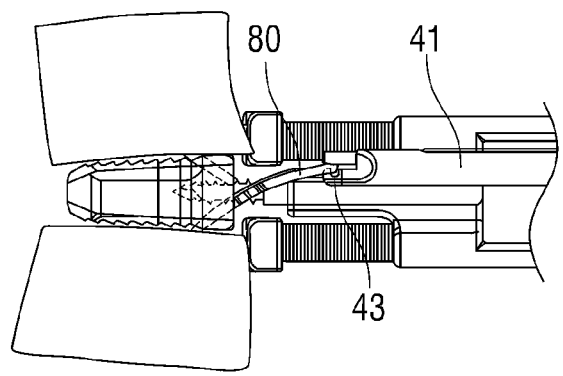
Figure 46:
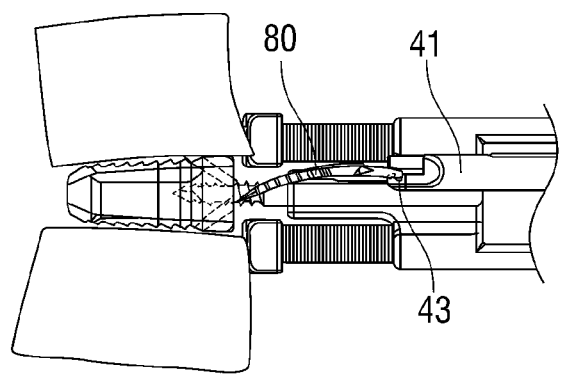

In the illustrated embodiments, handle (70) is screwed onto threads disposed along attachment adapter (47) until bearing surface (64) of extractor support (60) contacts bearing surface (75) of handle (70), for example as shown in FIGS. 42 and 43. Further rotation of handle (70) causes extractor shaft (41) to move linearly away from the implant (90), as depicted in FIG. 43. This linear movement of extractor shaft (41) causes hook to pull anchor (80) out of the vertebra and the implant, for example as shown in FIGS. 44-46. If necessary, sufficient force is applied to anchor (80) to overcome any latches (84) or other retention means holding the anchor in the implant. FIGS. 44-46 illustrate that the oblong channel in guide (13) permits hook (43) to rise and fall as necessary to accommodate the extraction path of anchor (80).

Figure 47:
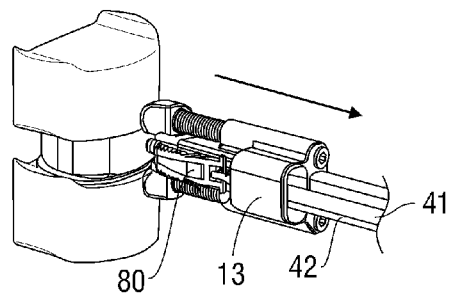
Figure 48:
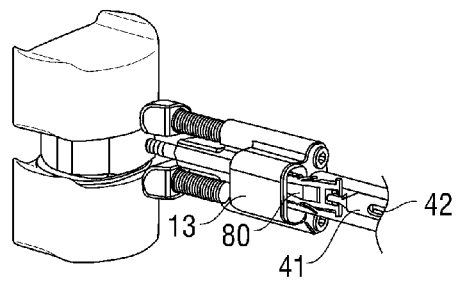
Figure 49:
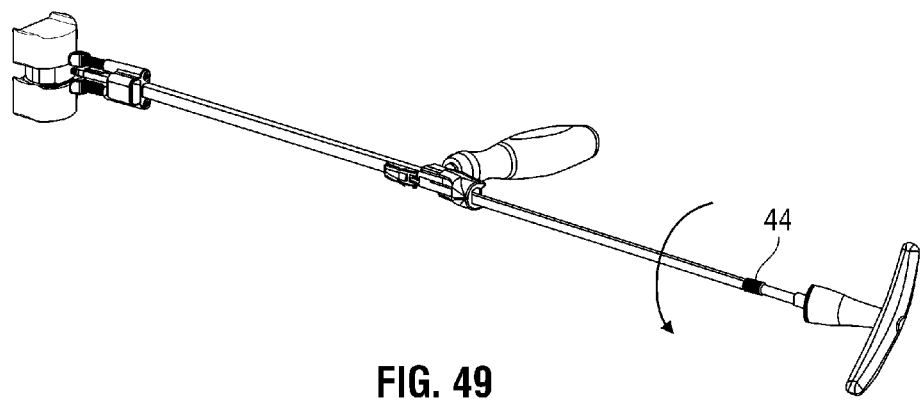

Anchor (80) can now be withdrawn through the channel in extractor guide (13). If necessary due to the relative widths of anchor (80) and the channel in guide (13), anchor (80) may be rotated by rotating shaft (41) and then withdrawn through the channel, for example as shown in FIGS. 47-48. When the anchor (80) is away from the surgical approach area, it can be removed from hook (43) by reversing the rotation of anchor attachment rod control (44), thus withdrawing anchor attachment rod (42) and opening attachment hook (43) to release anchor (80), for example as shown in FIG. 49. The foregoing method may be repeated for any additional anchors that need to be withdrawn.

The foregoing example of anchor extraction using embodiments of anchor removal instrument (1) previously described is merely representative. Various steps may or may not be required, or additional or modified steps may be required, depending on the particular embodiments of implants, anchors, and extraction tools used, and various embodiments of extraction tools may be used depending on the steps performed and the implants and anchors involved. It also should be noted that in multi-anchor implants, it may not be necessary to remove all anchors prior to removal of the implant. For example, an implant and associated anchors could be configured so that the implant could be removed after extraction of one anchor (80) by pulling on the implant and causing the implant itself to extract the remaining anchor during withdrawal of the implant.

After appreciating this disclosure, those of skill in the art will recognize that the steps of the various methods, processes, and other techniques disclosed herein need not be performed in any particular order, unless otherwise expressly stated or logically necessary to satisfy expressly stated conditions. In addition, after appreciating this disclosure those skilled in the art will recognize that the invention may be embodied in a variety of different forms and that various changes, substitutions, and alterations can be made without departing from the spirit and scope of the invention. References herein to surfaces or other structures as "upper," "top," "lower," "bottom," "inner," "outer," or having a "height," "width," or "length," and directional references such as "horizontal" and "vertical," are generally arbitrary and for convenience only, and those of skill in the art will recognize after appreciating this disclosure that such designations appropriately may be reoriented in particular embodiments. The described embodiments are illustrative only and are not restrictive, and the scope of the invention is defined solely by the following claims.

The invention claimed is:

1. A vertebral implant system comprising
an implant anchor;
an implant having a pathway configured to receive the anchor from the side of the implant and guide the anchor into a vertebral endplate; and
a tool for removing the anchor from the intervertebral implant comprising:
an elongated support comprising a vertebral body bumper at a first end of the support and a stabilization handle disposed proximal to a second end of the support;
a coupler configured to fix the support to the implant;
an elongated extractor comprising an anchor attachment at one end of the extractor and an extraction actuator;
an extractor guide disposed along the support proximal to the first end of the support; and
an extractor support disposed along the support proximal to the second end of the support.

2. The system of claim 1 in which the coupler comprises a rod with screw threads on one end and a drive adapter on the other end.

3. The system of claim 2 in which the elongated support further comprises a tube extending between the first end of the support and the second end of the support, the tube configured to hold the coupler.

4. The system of claim 1 further comprising a drill.

5. The system of claim 4 in which the elongated support further comprises a head and a removable drilling guide receivable in the head.

6. The system of claim 1 in which the anchor attachment comprises a hook and a closure configured to grasp an anchor.

7. A vertebral implant system comprising
an implant anchor;
an intervertebral implant having a pathway configured to receive the anchor from the side of the implant and guide the anchor into a vertebral endplate; and
an instrument for removing the anchor from the intervertebral implant comprising:
a support comprising a vertebral body bumper and a stabilization handle;
a coupler configured to fix the support to the implant;
an extractor comprising an anchor attachment and an extraction actuator; and
an extractor guide disposed along the support.

8. The system of claim 7 in which the coupler comprises a screw.

9. The system of claim 7 in which the anchor attachment comprises a clamp.

10. The system of claim 9 in which the clamp comprises a hook and a hook closure.

11. The system of claim 10 in which the hook closure comprises a sliding rod.

12. The system of claim 9 in which extraction actuator comprises a handle.

13. The system of claim 7 in which the extractor further comprises a rod extending between the anchor attachment and the extraction actuator.

14. A vertebral implant system comprising
an implant anchor;
an intervertebral implant having a pathway configured to receive the anchor from the side of the implant and guide the anchor into a vertebral endplate; and
an instrument for removing the anchor inserted into the intervertebral implant to retain the implant against a vertebral body, the instrument comprising:
an anchor extractor shaft having a first end configured with an anchor attachment and a second end longitudinally distal from the first end;
an anchor extractor shaft guide comprising
a channel configured to receive the anchor extractor shaft and permit rotational movement of anchor extractor shaft, and
an implant contact surface configured to abut the intervertebral implant when the anchor extractor shaft guide is placed for removal of the anchor; and
an operation handle connectable to the second end of the anchor extractor shaft and operable to extract the anchor.

15. The system of claim 14 further comprising threads for connection of the operation handle to the second end of the anchor extractor shaft.

16. The system of claim 15 further comprising a stabilization handle connectable to the anchor extractor shaft guide.

17. The system of claim 14 further comprising a removable drilling guide receivable in the channel.

18. A vertebral implant system comprising:
an implant anchor;
an implant having a pathway configured to receive the anchor from the side of the implant and guide the anchor into a vertebral endplate; and an implant anchor extractor tool comprising
a support,
a support retainer configured to hold the support fixed with respect to the implant,
an extractor having an anchor retainer, and
an extractor guide.

19. The system of claim 18 in which the extractor comprises guide surfaces configured to mate with complementary surfaces of the extractor guide.

20. The system of claim 19 in which the guide surfaces comprise a planar surface configured to mate with a complementary planar surface of the extractor guide.

21. The system of claim 18 in which the anchor retainer comprises a clamp comprising a hook and a tip of a slidable rod.

22. The system of claim 21 in which the sliding of the slidable rod is controlled by a rotating knob encircling the slidable rod.

23. The system of claim 18 in which the anchor comprises a body having at least one curved plate elongated along a longitudinal axis extending between a penetration end of the anchor and a driving end of the anchor, and a longitudinal rib extending along at least part of a face of the plate.

* * * * *